United States Patent [19]

Müller

[11] 4,056,636

[45] Nov. 1, 1977

[54] PROCESS FOR THE CONVERSION OF STARCH AND PROTEIN-CONTAINING CELLULOSIC WASTE PRODUCTS INTO NUTRIENTS RICHER IN PROTEINS

[76] Inventor: Hans Müller, Im Almendli, Erlenbach, Zurich, Switzerland

[21] Appl. No.: 570,456

[22] Filed: Apr. 22, 1975

[51] Int. Cl.$^2$ .............................................. C13K 1/06
[52] U.S. Cl. ................... 426/48; 195/31 R; 426/60; 426/656
[58] Field of Search ............... 426/48, 807, 52, 60, 426/78, 495, 656; 195/82, 105, 106, 31

[56] References Cited

U.S. PATENT DOCUMENTS

| | | | |
|---|---|---|---|
| 3,105,799 | 10/1963 | Tveit | 195/82 |
| 3,314,797 | 4/1967 | Hess et al. | 426/48 |
| 3,622,556 | 11/1971 | O'Connor | 260/123.5 |
| 3,939,281 | 2/1976 | Schwengers | 195/31 R |
| 3,953,296 | 4/1976 | Trutnovsky et al. | 195/127 |
| 3,958,015 | 5/1976 | Gay | 426/656 |

OTHER PUBLICATIONS

Micheals, "New Separation Technique for the CPI" Chemical Engineering Progress, (vol. 64, No. 12), 1968, pp. 31-43.

*Primary Examiner*—Raymond N. Jones
*Assistant Examiner*—C. A. Fan
*Attorney, Agent, or Firm*—Michael J. Striker

[57] ABSTRACT

Processes for the conversion of defatted cellulosic starch and protein-containing waste products, such as bran from cereal and flour mills and broken pieces and crumbs of baked goods from bakeries, into nutriments richer in proteins by dispersing in water the defatted waste products in comminuted form, subjecting the dispersion of the waste products in water to hydrolysis to convert the starches therein to glucose or other fermentable sugars, separating the glucose-containing liquid from the remaining solids by ultrafiltration, aerobically cultivating in the said glucose-containing liquid a yeast such as Candida utilis or a bacterium that ferments and utilizes glucose for growth and subsequently recovering from the fermented liquid the protein-containing yeast or bacterium that was grown therein.

3 Claims, No Drawings

PROCESS FOR THE CONVERSION OF STARCH AND PROTEIN-CONTAINING CELLULOSIC WASTE PRODUCTS INTO NUTRIENTS RICHER IN PROTEINS

BACKGROUND OF THE INVENTION

The present invention pertains to processes for the utilization of cellulosic starch and protein-containing waste products such as bran from cereal and flour mills and broken pieces and crumbs of baked goods from bakeries by converting the starch therein into protein-containing nutriments and supplements for animal feeds that are richer in proteins and accordingly more valuable than the original waste products.

In the production of cereal products, large quantities of waste products are produced which are used almost exclusively for animal feeds that nonetheless have inferior nutritional value. Considerable quantities of such cellulosic starch and protein-containing waste products are produced, for example, in the production of baked goods such as biscuits and crackers in bakeries. Furthermore, such bran is also produced in the milling of flour and other cereals.

Processes are known for the conversion of starches and starch-like substances into protein-containing plants, such as yeast cells or solids. One such process, which is described in U.S. Pat. No. 3,105,799, consists in symbiotically cultivating in a substratum consisting essentially of potatoes or similar vegetable material containing starch with two microorganisms, namely, one which hydrolyzes starch, such as Endomycopsis fibuliger, and a sugar-fermenting yeast, and separating the yeast plants that were grown therein during the fermentation, which yeast plants can be used as a nutriment. Such waste products, however, also contain a substantial portion of highly valuable proteins which had heretofore been overlooked or ignored.

Processes have also been described for the recovery of proteins by ultrafiltration but such processes have been heretofore used chiefly in the dairy industry, for example, for recovery of proteins from milk, for example, in an apparatus such as is described in German published application No. 2,220,308.

SUMMARY OF THE INNVENTION

The principal object of the present invention is to provide a process for the production of valuable proteins or protein-containing nutrients from the aforementioned cellulosic starch and protein-containing waste products. Other objects and advantages of the invention, some of which are referred to hereinafter, will be obvious to those skilled in the art to which it pertains.

The foregoing object is achieved in accordance with the processes of the present invention, in which process the cellulosic starch and protein-containing waste product is first subjected to hydrolysis to convert the starches therein into glucose or other fermentable sugars, the resulting suspension is then subjected to ultrafiltration to separate the glucose-containing liquid from the protein-containing solids remaining therein. These protein-containing solids are also valuable nutriments. Thereafter the glucose-containing liquid is inoculated with a yeast such as *Candida utilis*, *Saccharomyces cerevisiae* or *Hansenula polymorpha*, or a species of *Lactobacillus* or *Aerobacter* bacteria that has been approved by the Food and Drug Administration for the production of nutriments, and the yeast or bacterium is aerobically cultivated therein. The yeast or bacterium that has been grown therein is then recovered by conventional methods. Both the yeast or bacterial plants that are thus grown, as well as the protein-containing solids that have been recovered in the ultrafiltration step, are valuable sources of protein and may be used not only for the production of animal feeds and fodder but also in human nutrition.

DETAILED DESCRIPTION AND PREFERRED EMBODIMENTS OF THE INVENTION

The invention is described further in connection with the examples which follow, which were selected solely for purposes of illustration and consequently are not to be construed as restrictive of the invention or its scope.

EXAMPLE 1

The general procedure for carrying out the process of my invention that is described in this example is a preferred method and is used in all of the subsequent examples that are referred to hereinafter.

One thousand (1000) grams of comminuted defatted zwieback crumbs were stirred into 3 liters of water in an autoclave to which 30 milliliters of concentrated hydrochloric acid (32% by weight of hydrogen chloride) was then added and the suspension was then heated at a temperature of 120° C for a period of approximately 2 hours, during which period it was stirred vigorously. At the end of this period, no starch could be detected in the mixture, indicating that it had been completely hydrolyzed. The resulting hydrolyzed mixture contained between 500 and 700 grams of glucose which was identified by chromatography. This mixture was then diluted with tap water to a volume of approximately 20 liters and subjected to ultrafiltration to separate and recover the protein-containing solids therefrom. Suitable ultrafiltration apparatus that is commercially available may be used for this purpose. The filtrate contains between 500 and 700 grams of fermentable glucose and has a concentration of between 25 and 30 grams per liter.

Three (3) liters of this glucose solution is then placed into a fermentor having a capacity of 7 liters and 15 milliliters of concentrated phosphoric acid (85% by weight of phosphoric acid) and nutrient salts that are required for growth were added thereto. Ammonium hydroxide was then added to the solution in such an amount as to bring the hydrogen-ion concentration of the solution to a value corresponding to a pH of 4.0 and the mixture was sterilized by heating it for 20 minutes at a temperature of 121° C, after which it was cooled to a temperature between 28° and 32° C and inoculated with a culture of *Candida utilis* yeast in an amount equivalent to between 2 and 5 grams (dry weight) of the yeast. The fermentation is then continued at a temperature of approximately 32° C while air at a rate between 0.5 to 1.0 vvm (liters per minute and working volume) is bubbled through the fermenting culture for a period of approximately 25 hours, or until all of the glucose has been completely consumed by the yeast for its growth and additional yeast cells have been produced.

After the fermentation has been completed, the entire mass of solid living yeast cells was separated in a centrifuge, washed with water, having a solids content between approximately 16 and 20% on a dry-weight basis. The yeast solids were then dried further to a solids content of approximately 93% in a drum drier. The drying could alternatively have been effected by spray-drying.

The yield of solid yeast cellular matter on a dry-weight basis was 50 grams which is between 45 and 48% relative to the weight of the glucose that was fermented. The yeast thus produced by cultivation of Candida utilis contained 7% by weight of water, approximately 50% by weight of protein (determined by the Kjeldahl method), approximately 30% by weight of nonnitrogeneous compounds, 5.1% by weight of fat, and 7.6% by weight of ash. It had a nucleic acid content of 9.3% by weight and the amino acid content of the proteins in the yeast were as follows: aspartic acid 10.4%, threonine 5.8%, serine 6.0%, glutamic acid 12.4%, proline 3.5%, glycine 5.1%, alanine 6.7%, valine 5.3%, methionine 2.0%, isoleucine 4.7%, leucine 7.9%, tyrosine 5.3%, phenylalanine 7.1%, lysine 8.0%, histidine 2.5%, arginine 5.8%, and tryptophan 0.8%.

The yeast solids thus produced can be used as a protein-rich supplement for addition to poultry, cattle, and hog feeds in amounts between 10 and 30% by weight. It is also suitable for use as a yeast nutrient in human nutrition.

EXAMPLE 2

One thousand (1000) grams of finely ground defatted zwieback crumbs were stirred into 20 liters of water and the suspension was then made homogeneous by vigorous stirring. A small amount of alpha-amylase was then added to the suspension and the mixture was allowed to stand for such a period and at such a temperature that the starch therein was completely hydrolyzed. The resulting hydrolyzed mixture was then subjected to ultrafiltration as in Example 1 and the filtrate was inoculated with a culture of Candida utilis yeast as in Example 1. The fermentation and recovery of the yeast solids from the fermentation broth were completed as described hereinbefore in connection with Example 1.

EXAMPLE 3

Instead of using zwieback as in Example 1, 1000 grams of finely ground defatted cake crumbs which on a weight basis consisted of 4.9% water, 16.0% of sucrose, 1.5% of sodium chloride, and 77.6% of starch, were substituted therefor and in all other respects the procedure describe in Example 1 was repeated.

The yeast solids that were recovered did not differ to any substantial extent from the product that was described in Example 1 and the amount that was obtained was equivalent to 55 grams on a dry-weight basis.

EXAMPLE 4

One thousand (1000) grams of defatted wheat bran were substituted for the zwieback crumbs that were used in Example 1 and the procedure therein described was repeated with essentially the same results.

Although alpha-amylase was used in Example 2, it is to be understood that other known starch-hydrolyzing enzymes may be substituted therefor. Other acids that are known to be capable of hydrolyzing starch may also be used instead of the hydrochloric acid that was used in Example 1.

Furthermore, instead of using an enzyme, the hydrolysis may be effected by cultivation in the dispersion of a microorganism that is known to be capable of hydrolyzing the starch, such as a microorganism of the group Endomycopsis, such as, for example, the species Endomycopsis fibuliger. The microorganism is then separated from the hydrolyzed dispersion before the dispersion is subjected to ultrafiltration or is separated with the other solids during the ultrafiltration step.

When bacteria are used instead of fungi as in Example 1, the fermentation is completed after a period of 20 hours at most.

When the cultivation or fermentation is conducted in a continuous manner with yeast, a residence period of the broth in the fermentor of approximately 4 to 5 hours must be allowed for completion of the fermentation, whereas a residence period of only 2 hours at most is required in a continuous bacterial fermentation.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A process for the recovery of high-protein materials from starch and protein-containing pieces and crumbs of broken baked goods from bakeries which process comprises
   dispersing said baked goods in comminuted form in water;
   subjecting said dispersion to an acid-, enzyme-, or microorganism-induced hydrolysis under suitable conditions sufficient to convert the starch in said dispersion to a fermentable sugar;
   thereafter separating and recovering protein containing solids from the hydrolyzed dispersion by means of ultrafiltration, and
   aerobically cultivating in the remaining sugar-containing liquid a yeast that is capable of fermenting the sugar-containing liquid and utilizing the sugar therein for growth, and
   finally recovering from the fermented liquid a high protein yeast formed by said fermentation whereby said protein containing solids and said high protein yeast are suitable for use in human and animal food products.

2. A process as defined in claim 1 in which the hydrolysis is effected by cultivation in the dispersion of a microorganism that is capable of hydrolyzing starch and the microorganism is separated from the hydrolyzed dispersion before the dispersion is subjected to ultrafiltration.

3. A process as defined in claim 1 in which the baked goods are defatted zwieback.

* * * * *